United States Patent
Vo et al.

(10) Patent No.: US 12,048,534 B2
(45) Date of Patent: Jul. 30, 2024

(54) SYSTEMS AND METHODS FOR SECURING A TISSUE SITE TO A SENSOR

(71) Applicant: Willow Laboratories, Inc., Irvine, CA (US)

(72) Inventors: Hung The Vo, Fountain Valley, CA (US); Cristiano Dalvi, Lake Forest, CA (US); Kevin Hughes Pauley, Lake Forest, CA (US)

(73) Assignee: Willow Laboratories, Inc., Irvine, CA (US)

( * ) Notice: Subject to any disclaimer, the term of this patent is extended or adjusted under 35 U.S.C. 154(b) by 601 days.

(21) Appl. No.: 17/192,627

(22) Filed: Mar. 4, 2021

(65) Prior Publication Data

US 2021/0275101 A1    Sep. 9, 2021

Related U.S. Application Data

(60) Provisional application No. 62/985,164, filed on Mar. 4, 2020.

(51) Int. Cl.
| | | |
|---|---|---|
| *A61B 5/1455* | (2006.01) | |
| *A61B 5/00* | (2006.01) | |
| *A61B 5/02* | (2006.01) | |
| *A61B 5/0205* | (2006.01) | |

(52) U.S. Cl.
CPC ............. *A61B 5/1455* (2013.01); *A61B 5/02* (2013.01); *A61B 5/0205* (2013.01); *A61B 5/6832* (2013.01); *A61B 5/6839* (2013.01)

(58) Field of Classification Search
CPC ....... A61B 5/1455; A61B 5/02; A61B 5/0205; A61B 5/6832; A61B 5/6839; A61B 5/14552; A61B 5/6826; A61B 5/0075
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| 5,319,355 A | 6/1994 | Russek | |
| 5,337,744 A | 8/1994 | Branigan | |
| 5,341,805 A | 8/1994 | Stavridi et al. | |
| 5,377,676 A | 1/1995 | Vari et al. | |
| 5,431,170 A | 7/1995 | Mathews | |
| 5,436,499 A | 7/1995 | Namavar et al. | |
| 5,456,252 A | 10/1995 | Vari et al. | |

(Continued)

FOREIGN PATENT DOCUMENTS

WO    WO 2010/082444    7/2010

OTHER PUBLICATIONS

Gannon, Mary, "What are the benefits of spring-loaded contacts?", ConnectorTips.com, Sep. 7, 2016, pp. 6.

*Primary Examiner* — Eric F Winakur
*Assistant Examiner* — Abid A Mustansir
(74) *Attorney, Agent, or Firm* — Knobbe, Martens, Olson & Bear, LLP

(57) ABSTRACT

Systems, methods, and apparatuses for enabling non-invasive, physiological sensors to obtain physiological measurements from a region of tissue of a patient are disclosed. Anchoring components can attach to patient tissue sites and sensor heads such that the tissue sites do not move during sensing. Interlocking mechanisms maintain tissue sites within a limited range of horizontal movement and vertical distance from the sensor head.

18 Claims, 9 Drawing Sheets

(56) References Cited

U.S. PATENT DOCUMENTS

| | | |
|---|---|---|
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |

(56) References Cited

U.S. PATENT DOCUMENTS

| | | |
|---|---|---|
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Ai-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Ai-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Ai-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Ai-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B2 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |

(56) References Cited

U.S. PATENT DOCUMENTS

| | | |
|---|---|---|
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0208169 A1* | 11/2003 | Chaiken .......... A61B 5/0053 600/306 |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |

(56) References Cited

U.S. PATENT DOCUMENTS

| | | |
|---|---|---|
| 2005/0234317 A1 | 10/2005 | Kiani |
| 2006/0073719 A1 | 4/2006 | Kiani |
| 2006/0189871 A1 | 8/2006 | Al-Ali et al. |
| 2007/0027376 A1 | 2/2007 | Todokoro et al. |
| 2007/0073116 A1 | 3/2007 | Kiani et al. |
| 2007/0123763 A1* | 5/2007 | Al-Ali .................. A61B 5/6832 600/344 |
| 2007/0180140 A1 | 8/2007 | Welch et al. |
| 2007/0244377 A1 | 10/2007 | Cozad et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2017/0024748 A1 | 1/2017 | Haider |
| 2017/0231566 A1* | 8/2017 | Klimek ................ A61B 5/6802 600/324 |
| 2017/0251974 A1 | 9/2017 | Shreim et al. |
| 2018/0242926 A1 | 8/2018 | Muhsin et al. |
| 2018/0247712 A1 | 8/2018 | Muhsin et al. |
| 2019/0320906 A1 | 10/2019 | Olsen |
| 2020/0060869 A1 | 2/2020 | Telfort et al. |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0329983 A1 | 10/2020 | Al-Ali et al. |
| 2020/0329993 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256835 A1 | 8/2021 | Ranasinghe et al. |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |

\* cited by examiner

SYSTEMS AND METHODS FOR SECURING A TISSUE SITE TO A SENSOR

CROSS REFERENCE TO RELATED APPLICATIONS

The present application claims priority to U.S. Provisional Patent Application No. 62/985,164, filed on Mar. 4, 2020, the contents of which are incorporated by reference herein.

FIELD

The present disclosure relates to physiological monitoring. More specifically, this disclosure relates to systems, methods, and apparatuses for reducing error in repeated non-invasive physiological measurements.

BACKGROUND

Non-invasive physiological monitoring may require placement of a non-invasive sensor on a tissue site. Changes in positioning of the sensor of the tissue site can introduce error to measurements due to variations in tissue composition.

SUMMARY

In some examples, a system for aligning a tissue site of a patient to a sensor is disclosed. The system can include: a first anchoring component configured to couple to the tissue site of a patient, wherein the first anchoring component can include: a first surface configured to couple to the tissue site; a first opening configured to allow at least one non-invasive sensor to perform a physiological measurement of the tissue site; and at least one securing component to secure the first anchoring component to a second anchoring component associated with the at least one non-invasive sensor such that the tissue site is maintained within a range of vertical distances from the non-invasive sensor and is secured to disallow horizontal movement within a range of horizontal distances.

The first surface can couple to the tissue site using an adhesive.

The adhesive can be configured to couple the first surface to the tissue site for a period comprising at least one day.

The first surface can have a curvature similar to that of the tissue site.

The at least one securing component can include one or more latches, slides, or snaps.

The at least one securing component can include at least one wall of the first opening having a first slope, and the second anchoring component can include at least one wall having the first slope.

The at least one securing component can be configured to mate with a mating component associated with the second anchoring component.

The second anchoring component can be configured to mate with a third anchoring component.

The third anchoring component can include a portion of the non-invasive sensor.

The first opening can include a keyhole shape.

In some examples, a method for aligning a tissue site to a sensor is disclosed. The method can include: attaching a first anchoring component to the tissue site; connecting the first anchoring component to a second anchoring component attached to a sensor head, such that the sensor head is aligned with an opening in the first anchoring component; and securing the first and second anchoring components such that the tissue site maintains generally a vertical distance away from the sensor head.

Connecting the first anchoring component to the second anchoring component can include moving at least one catch into at least one slide.

Connecting the first anchoring component to the second anchoring component can include moving the second anchoring component into a keyhole fitting.

Securing the first anchoring component to the second component can be completed by a user moving the tissue site in relation to the second anchoring component.

The first and second anchoring components can be secured such that the tissue site generally restricts horizontal movement of the tissue site.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

The following drawings and the associated descriptions are provided to illustrate embodiments of the present disclosure and do not limit the scope of the claims.

DETAILED DESCRIPTION

Overview

Examples disclosed herein relate to systems and methods for anchoring a tissue site for a physiological measurement. These systems can be used, for example, on transmission-based spectroscopy technologies or reflectance-based spectroscopy technologies.

Many devices place an alligator-type or clothespin-type clip to align a finger with a sensor for measuring physiological parameters. For example, current pulse oximetry and co-oximetry noninvasive sensors can require a user to place his or her finger in a clothespin-type clip. This action can require both hands of the patient or a clinician to ensure accurate placement. Additionally, placement accuracy of the emitter and detector windows relative to the patient's measurement site can be difficult to achieve with an alligator clip type sensor. Placement of the windows is important in obtaining a value when measuring.

The anchoring system described herein may improve the placement of transmission and reflectance based spectroscopic sensors at a patient tissue site. For example, in the case of a finger, the anchoring system may allow for consistent and ergonomic finger placement with relation to the sensor and more consistent sensor measurements due to ease of use and increased precision of tissue site placement.

In some examples, an anchoring system can include one or more anchoring components. At least one anchoring component can be configured to both couple to the tissue site of a patient and a component associated with a physiological sensor. The anchoring system may be configured to hold the tissue site in place using the anchoring component(s) while a physiological measurement is performed. Additionally or alternatively, the anchoring system can be configured to couple to a sensor head such that the same tissue site can be measured after removal and replacement of a tissue site in relation to the sensor.

In some examples, an anchoring component can include a tissue anchor, such as described with reference to FIG. 1. The tissue anchor can be configured to couple to one or more tissue sites, such as one or more types of fingers, such as a thumb, index finger, or ring finger. Additionally or alternatively, the tissue anchor can be configured to anchor a tissue site with respect to a sensor using one or more anchoring mechanisms such that the tissue site remains steady during measurement by the sensor and tissue placement is repeatable. Examples of anchoring mechanisms are discussed, for example, with reference to FIGS. 2 and 3A-B.

Example Anchoring System

Figure 1:
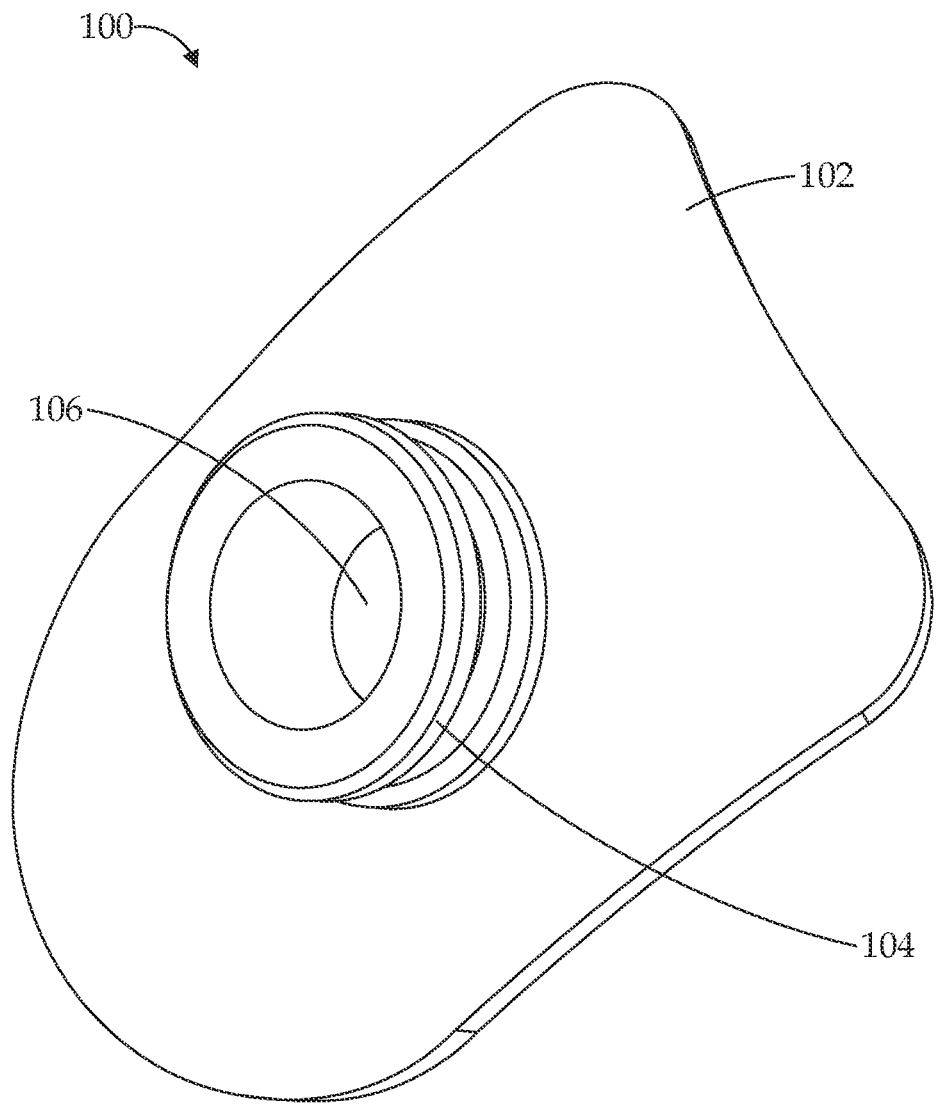
FIG. 1 shows a top view of an illustrative example of a tissue anchor, according to certain embodiments of the present disclosure.

FIG. 1 illustrates an embodiment of a tissue anchor 100, according to the present disclosure. The tissue anchor 100 can include at least one anchoring surface 102, one or more interlock components 104, and one or more openings 106. The illustration in FIG. 1 depicts just one example of the tissue anchor 100 and should be understood to not limit the shape of the anchoring surface 102, the type of interlock component 104, and the shape of the opening 106 for the sensor head.

A sensor head, such as described herein, can include components or aspects of a noninvasive sensor, invasive sensor, or minimally invasive sensor configured to measure one or more physiological parameters from a tissue site of a patient. A physiological parameter can include, but is not limited to, a heart rate, respiration rate, analyte concentration, temperature, the like or a combination thereof. In some examples, a noninvasive sensor can include an optical sensor, such as a Raman sensor, OCT sensor, or other optical sensor. In some examples, an invasive or minimally invasive sensor can include a blood analyte monitor, such as a continuous glucose monitor or other disease management system, such as described with reference to U.S. application Ser. No. 17/161,528, filed Jan. 28, 2021, titled "REDUNDANT STAGGERED GLUCOSE SENSOR DISEASE MANAGEMENT SYSTEM," the contents of which is hereby incorporated by reference in its entirety. It is of note that while in some examples reference may be made to a sensor, a sensor head, or other sensor components, systems and methods described herein can additionally or alternatively refer to other components or devices configured for close placement to a tissue site, such as a component configured to deliver medication to a user, such as an insulin pump, and the configurations disclosed herein may be used for attaching a medication delivery system to a user. Additionally or alternatively, systems and methods described herein may be applicable to any system that requires secure attachment of a device to a tissue site of a patient for a short or prolonged period of time.

An anchoring surface 102 may be configured to fit to a tissue site of a patient. A tissue site of a patient can include, but is not limited to, a nail bed, fingernail, toenail, abdomen, arm, or other tissue site suitable for measuring physiological parameters using a noninvasive, invasive, or minimally invasive physiological sensor. In some examples, the anchoring surface 102 may have a contour similar to a tissue site of a patient. For example, a tissue site may be a fingernail and the anchoring surface 102 may have a contour such that the anchoring surface 102 sits approximately flush against the fingernail. In some examples, the contour of the anchoring surface 102 can be fitted to a patient and/or a tissue site. For example, the anchoring surface 102 can be contoured to a particular fingernail of a patient, such as a patient's ring finger. In another example, the anchoring surface 102 can be contoured to fit more than one tissue site. For example, the anchoring surface 102 can be contoured generally to fit against more than one fingernail type, such as a thumb and ring finger or other combination of tissue sites. In some examples, the contour of the anchoring surface 102 may be molded to a particular tissue site. For example, the anchoring surface 102 may include one or more moldable materials. In another example, the anchoring surface 102 may be generically contoured to fit a generic tissue site type, such as a typical human thumb nail.

In some examples, one or more coupling materials can be applied to the anchoring surface 102 to improve the fit of the anchoring surface 102 to the tissue site. For example, the coupling material can include a gel, optical coupling material, or other moldable or semi-moldable material. In some examples, a coupling material may be configured to permanently or semi-permanently attach the anchoring surface 102 to the tissue site. Such a coupling material can include a glue, tape, or other attachment material.

The size of the anchoring surface 102 may be large enough to provide a coupling site to the tissue of the patient. For example, where the tissue site is a fingernail, the size anchoring surface 102 can be a sizable portion of the fingernail, such as 10%, 20%, 50%, or 80% of the nail bed or more or less of the nail bed. Additionally or alternatively, the size of the anchoring surface 102 may be large enough to couple with one or more sensor heads, such as described with reference to U.S. patent application Ser. No. 17/004,663, filed Aug. 27, 2020, titled "NON-INVASIVE MEDICAL MONITORING DEVICE FOR BLOOD ANALYTE MEASUREMENTS," the contents of which is hereby incorporated by reference in its entirety. For example, the anchoring surface 102 can be at least the size of a sensor head configured to couple with the anchoring component.

An interlock component 104 can include a mechanism to aid in coupling a sensor to the tissue anchor 100. The interlock component 104 can have any number of interlock styles, including, but not limited to, keyhole interlocks, hinged interlocks, bolt interlocks, etc. As described with reference to FIGS. 2 and 3A-B, the interlock component 104 can couple with an interlocking mechanism 200 that attaches to a sensor, such that the tissue anchor 100 may be coupled with a sensor head. In some examples, the tissue anchor 100 can include more than one interlock component 104 for more than one attachment site to a sensor head. In another example, the tissue anchor 100 can include multiple interlock components 104 for coupling with more than one sensor head, such as more than one sensor or sensor head type.

The opening 106 can be an appropriate shape and size to couple with a sensor head such that the sensor head can sense the tissue site directly. For example, an opening 106 may allow for a clear optical path to the tissue site to perform a physiological measurement with one or more sensors. The opening 106 can be positioned at any location in the tissue anchor 100 so as to provide access to the tissue site. In some examples, there may be more than one opening 106 to provide multiple points of access to the tissue site. The size of the opening 106 can be of a suitable size for a required measurement of the tissue site. For example, a sensor may require a one square cm^2 area to perform a measurement. The opening 106 may be at least the one square cm^2 to allow for a proper measurement using the appropriate sensor. In another example, the opening 106 may be large enough for more than one sensor to perform a measurement. For example, a sensor head can include multiple sensor types. Each sensor type may require the same or a different area of the tissue site to perform measurements. The opening 106 may be of sufficient size to accommodate one or all of the coupled sensors. In another examples, the tissue anchor 100 may be configured to couple to more than one sensor head type requiring different area amounts of tissue site for measurement. The opening 106 may be large enough to accommodate one or more of the coupled sensor head types.

A shape of the opening 106 can be any number of shapes, such as a circle, square, triangle, or other geometry. The shape of the opening 106 can include a shape associated with the interlock mechanism 104. For example, the shape of the opening may mirror the shape of the interlock mechanism 104. In another example, the shape of the opening 106 may mirror the shape of one or more sensor heads configured to couple to the tissue anchor 100. For example, a sensor head may be circular and the opening 106 may also be circular.

Figure 2:
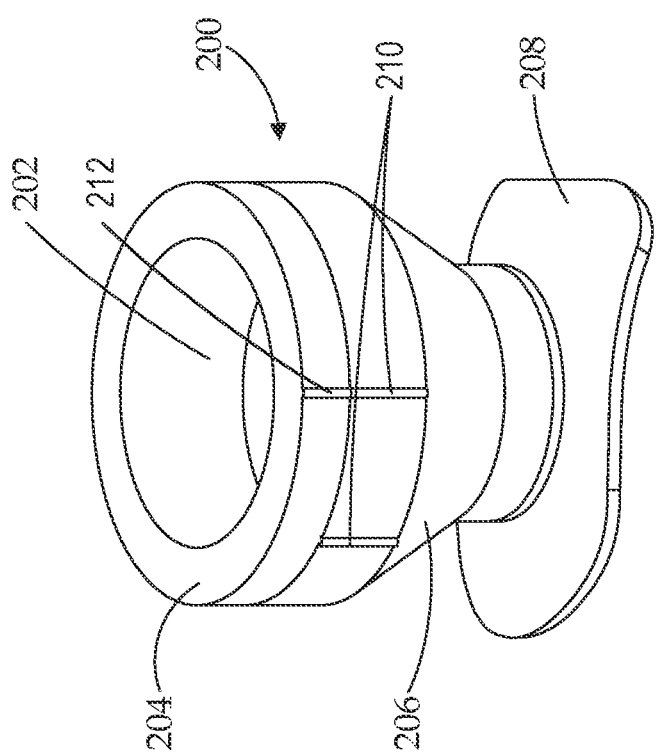
FIG. 2 illustrates a tissue anchor attached to an interlocking mechanism and sensor receiver, according to certain embodiments of the present disclosure.

FIG. 2 depicts an exemplary embodiment of a tissue anchor 208 coupled to an interlocking mechanism 200. An interlocking mechanism 200 can include one or more components, such as a tissue anchor attachment 206 and a sensor head attachment 204.

The tissue anchor attachment 206 can couple with the tissue anchor 208 via an interlocking mechanism, such as interlock component 104 illustrated in FIG. 1. For example, the tissue anchor attachment 206 can be if a size and shape to mate with the interlock component 104 of a tissue anchor 208. Any number of mating mechanisms may be used to mate the tissue anchor attachment 206 with the interlock component 104, such as described below with reference to FIGS. 3A-3D.

In some examples, the tissue anchor component 206 may be coupled to or be a part of a sensor head (not shown). In other examples, the interlocking mechanism 200 can include a sensor head attachment 204. The senor head attachment 204 can be part of or couple with a sensor head (not shown). For example, the sensor head attachment 204 can be permanently or removably attached to a sensor head so as to allow the sensor head to couple to the tissue anchor attachment 206 or tissue anchor 208. The sensor head attachment 204 can be configured to mate with the tissue anchor 208 and/or tissue anchor attachment 206. For example, the sensor head attachment 204 can be configured to removably lock onto the tissue anchor attachment 206 or otherwise secure the sensor head to the tissue anchor attachment 206 or tissue anchor 208.

In some examples, the sensor head attachment 200 may be of a size and shape to receive sensor head and/or lock a sensor head in place. For example, the interlocking mechanism 200 may have a sensor window 202 to receive a sensor head. The sensor window 202 can align with the tissue anchor opening 106 (such as shown, for example in FIG. 1) such that the sensor head can access the tissue site. Additionally or alternatively, the sensor window 202 and/or sensor head attachment 204 can be configured to fit around one or more sensor heads (not shown). In some examples, the sensor head attachment 204 and/or sensor window 202 may be interchangeable based on which sensor a user desires to couple to the tissue site or measure the tissue site. For example, the sensor head attachment 204 may be of a different size or shape according to the sensor head or sensor head type in use.

The tissue anchor attachment 206 and sensor head attachment 204 may contain markings 210 or other indicators to signify whether the components are in a locked or unlocked position. For example, the tissue anchor attachment 206 or other component of the interlocking mechanism 200 may be configured to lock onto another component. The locking mechanism may have an open and a close configuration. In an open configuration, a first marking 210 of a first mating component, such as, for example, a tissue anchor component 206, may align with another marking 212 of a second mating component, such as, for example a sensor head attachment 204. In a closed configuration, a second marking 210 of a first mating component, such as, for example, a tissue anchor component 206, may align with another marking 212 of a second mating component, such as, for example a sensor head attachment 204. However, other markings or indicators of alignment, attachment, or locking state are possible.

Though the illustration depicts an interlocking mechanism with more than one component, the interlocking mechanism can be one component or comprised of multiple components. It should also be understood that, in the case of various components, each component can be separated completely or merely have their positions adjusted relative to each other. The interlocking mechanism 200 may be operated automatically, semi-automatically, manually, or mechanically.

Example Coupling Components

Figure 3A:
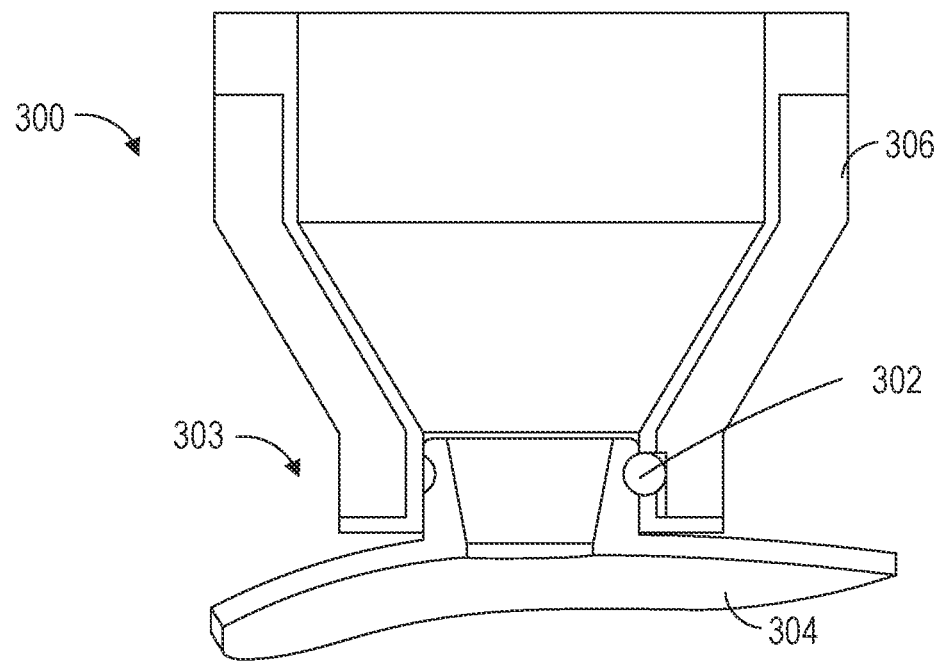
FIGS. 3A and 3B show a cross-section and top-down view respectively of an example interlocking mechanism in a locked position, according to some embodiments of the present disclosure.
Figure 3B:
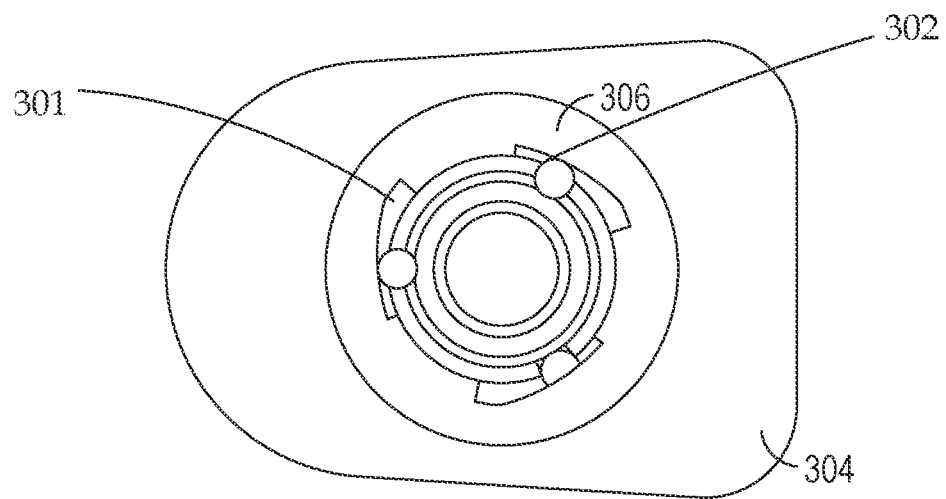
Figure 3C:
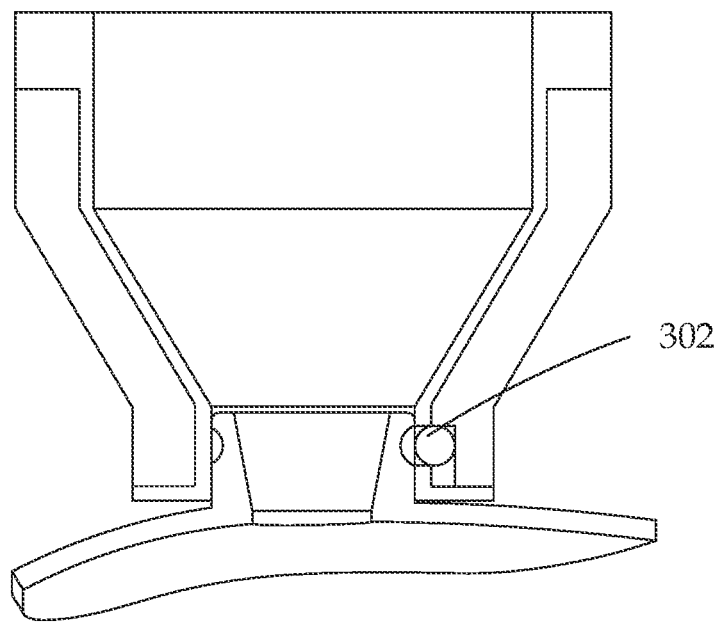
FIGS. 3C and 3D show a cross-section and top-down view respectively of the interlocking mechanism of FIGS. 3A and 3B in an unlocked position.
Figure 3D:
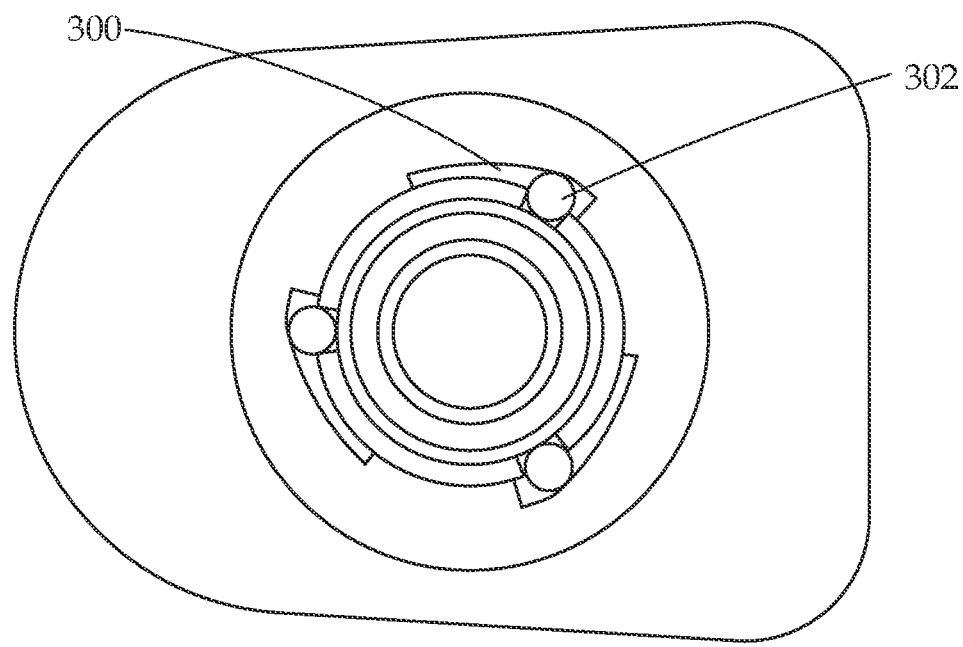

FIGS. 3A-3D illustrate example views of example interlocking components that may be part of an anchoring system. FIGS. 3A and 3B illustrate interlocking components 300 in an open configuration and FIGS. 3C and 3D illustrate interlocking components 300 in a locked configuration.

An interlocking mechanism 300 can include one or more interlocking components 303. The interlocking components 303 can include mating components, such as at least one catch 302 and at least one slide 301 or other components for maintaining the position and orientation of two or more components of the anchoring system. In some embodiments, the number of catches 302 may match the number of slides 301. In other examples, there may be a different number of catches 302 than slides 301. For example, an interlocking component may include multiple slides 301 and a single catch 302. In another example, an interlocking component may include multiple catches 302 and a single slide 301. Additionally or alternatively, there may be more than one type of mating component for maintaining a position and orientation of two or more portions of the anchoring system. For example, the interlocking components 303 can include some combination of catches and slides, threaded components, clips, latches, teethed components, grooved components, locking rings, pins, tightening components, or other securing components. Additionally or alternatively, a coupling may be accomplished by matching a first geometric shape of a first component with a second geometric shape of a second component, as discussed with reference to FIGS. 4A and 4B, below.

In some examples, slide 301 can be an elongated piece that contacts the catch 302. The slide 301 and catch 302 can remain in contact as the components transition between a locked and unlocked position. The slide 301 may contain a groove on one end that is shaped to accept the catch 302. Though the illustration shows a round catch 302, it is to be understood that the catch 302 can be any shape.

In some examples, the mating components may be part of different interlocking components. For example, a tissue anchor 304 can include one or more slides 301 and/or one or more catches 302. Additionally or alternatively, a sensor attachment 306 can include one or more mating slides 301 and/or catches 302. However, other mating components are possible. For example, a first interlocking component, such as a sensor attachment 306, may have one or more female and/or male mating components. In another example, a second interlocking component, such as a tissue anchor 304 may have one or more female and/or mating components that may mate with the mating components of the first interlocking component. For example, where the mating components include a catch 302 and a slide 301, a catch 302 may fit into a slide 301.

FIGS. 3A and 3B show the interlocking mechanism 300 in a locked position. For example, where the interlocking mechanism 300 includes slide 301 and catch 302 components, the catch 302 may be in the groove on the slide 301. In the locked position, the interlocking mechanism 200 may attach to the tissue anchor 100 (such as illustrated in FIG. 1) such that the interlocking mechanism 200 and tissue anchor 100 cannot be easily separated. Further, in the locked position, the tissue anchor 100 may not move independently from the interlocking mechanism 200.

FIGS. 3C and 3D show the interlocking mechanism 300 in an unlocked position. When the interlocking mechanism 200 is in the unlocked position, the catch 302 may not be in the groove on the slide 301. In the unlocked position, the interlocking mechanism 200 can be separated from the tissue anchor 100 and each piece can move independently.

The interlocking mechanism 200 can transition between a lock and unlocked position either manually or mechanically. Although FIGS. 3A-3D depict an interlocking mechanism that can be locked and unlocked through a twisting motion, it is to be understood that different types of interlocking mechanisms can be locked or unlocked through any variety of methods.

Example Keyhole Coupling

Figure 4A:
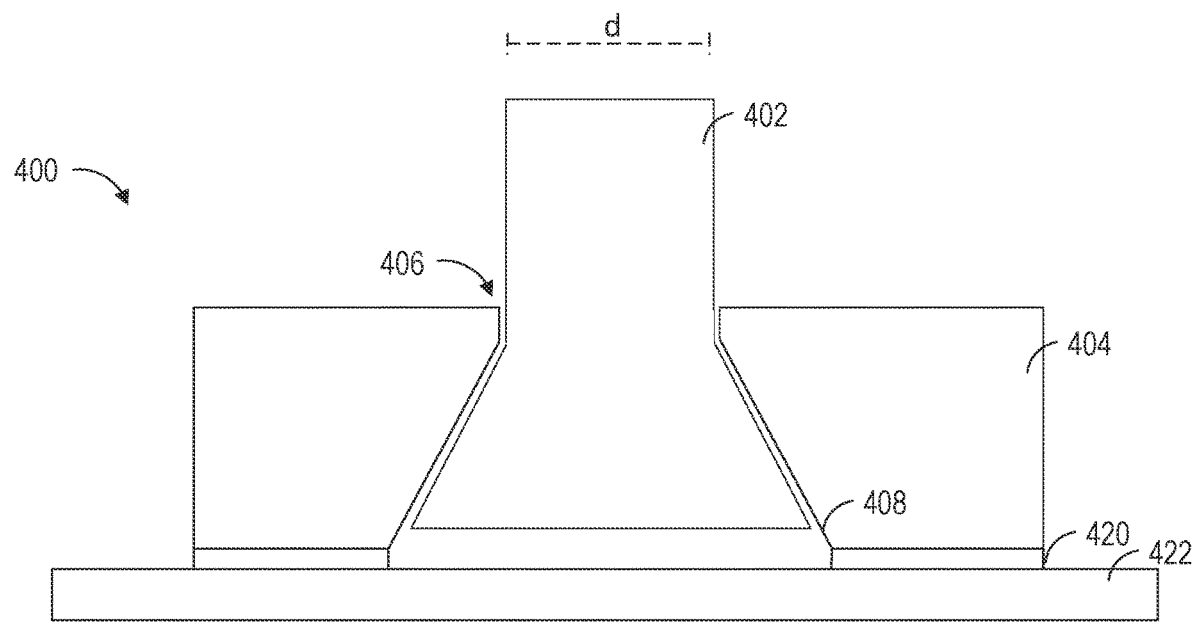
FIG. 4A shows a cross-section view of another interlocking mechanism.
Figure 4B:
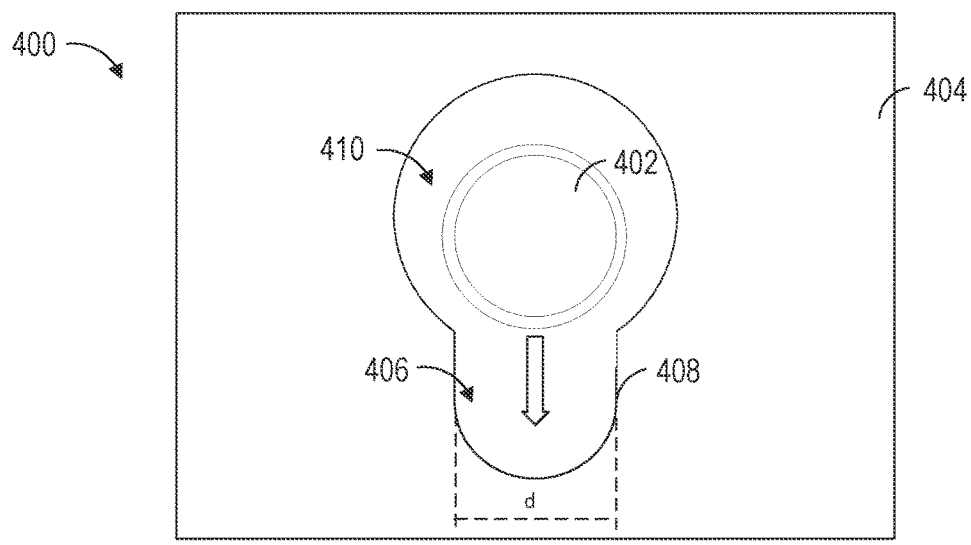
FIG. 4B shows a top-down view of the interlocking mechanism of FIG. 4A.

FIGS. 4A and 4B illustrate an example configuration of an anchoring system 400 that may include a keyhole locking mechanism. For example, a tissue anchor 404 may mate to an interlock component 402 associated with a sensor head. The tissue anchor 404 may be attached to a tissue site 422 via one or more coupling materials 420 disposed on the tissue site 422 or tissue anchor 404. The tissue site 502 may be, for example, a portion of a fingernail.

The tissue anchor 404 can include a mating structure 408 and one or more open areas 406, 410. An open area 406 can be of a suitable size and shape through which a sensor, such as a Raman sensor, can measure physiological parameters. For example, the open area 406 can be large enough to include the spot size of an excitation source that may be part of the Raman sensor. Additionally or alternatively, the open area 406 can be large enough to allow for the excitation source of the sensor to scan the tissue site or to account for movement of the excitation source during use or manufacture. In some examples, the open area 406 can be part of the mating structure 408 such that the one or more portions of the open area 406 can be capable of accepting one or more portions of the interlocking component 402. In some examples, the open area may have a diameter d substantially similar to the diameter of an interlock component 402 such that the interlock component 402 fits snugly in the open area 406.

Additionally or alternatively, an open area 410 may connect with the open area 406. The open area 410 may be of a different size and shape than the open area 406 such that an interlock component 402 may be received without significantly restraining the interlock component 402. Advantageously, the open area 410 may thus allow the tissue anchor 404 to receive the interlock attachment 402 more easily so that a user can move the interlock attachment 402 into place in the open area 406, such as illustrated in FIG. 4B.

A mating structure 408 of the tissue anchor 404 can be a structure capable of mating with an interlock component 402 that may be associated with a sensor head. For example, the mating structure 408 may have a geometric shape, such as a truncated cone. An associated interlock component 402 may also have a truncated cone shape. The shapes and sizes of the interlock component 402 and mating structure 408 may mate such that the position or orientation of the interlock component 402 may be substantially secured in a vertical and/or horizontal direction with respect to the tissue site 422.

The tissue anchor 404 can be coupled to the tissue site of a patient or user by any suitable means. For example, the tissue anchor 404 can be attached to the tissue site of a patient using a coupling material 420, such as a permanent or temporary adhesive, by permanent or temporary implantation, via a wearable device, or other suitable means of temporarily, semi-permanently, or permanently securing a component to a tissue site. In some examples, the tissue anchor 404 may be secured to a tissue site of a patient via a semi-permanent adhesive capable of securing the attachment component for a day or more. For example, the tissue anchor 404 may be secured to a tissue site with a medical adhesive, glue, tape, or other means of adhering components to a tissue site.

Example Sensor Head Attachment

Figure 5:
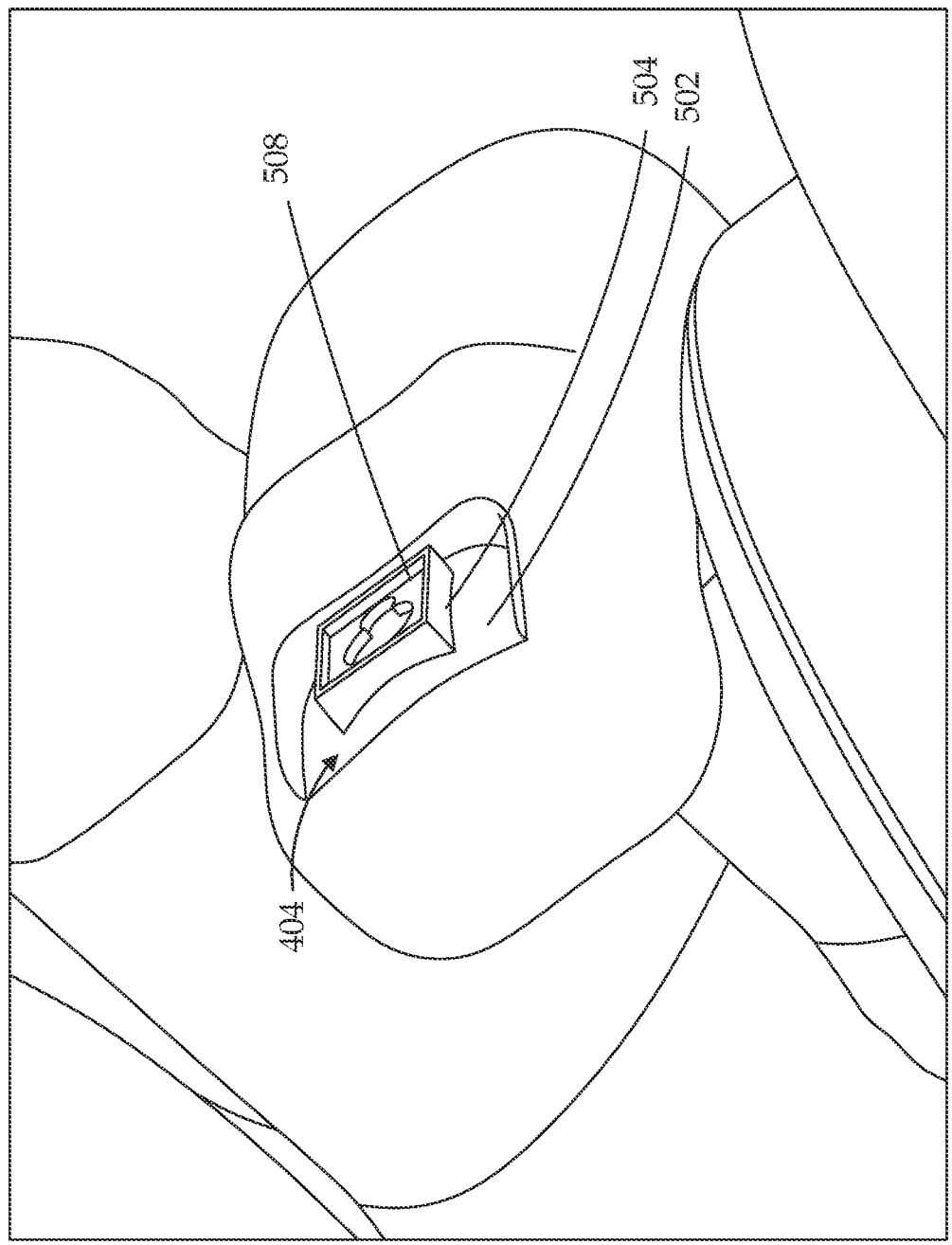
FIG. 5 shows another illustrative example of a tissue anchor, according to certain embodiments of the present disclosure.

FIG. 5 illustrates an example placement of a tissue anchor 404 that may mate with one or more components of a sensor head on a tissue site. In the illustrated example, the tissue site can include a portion of a fingernail 502. The tissue anchor 404 may be secured onto the fingernail 502 using, for example, a coupling material 420, such as described above. As described above, the tissue anchor 404 can include a surface 504 having a contour substantially similar to the tissue site 502 so as to allow for the tissue anchor 404 to comfortably sit on the tissue site 502.

The tissue anchor 404 can include an attachment structure 508. The attachment structure 508 can include a form and structure capable of mating with an interlock component associated with a sensor head. For example, the attachment structure 508 can include a central raised portion capable of fitting into a mating cavity of similar size and shape to the central raised portion. Additionally or alternatively, the attachment structure 508 can include one or more walls capable of securing the tissue anchor 500 within a mating cavity that may be part of an interlocking component (such as the interlocking component 602 of FIG. 6). The tissue anchor 500 can receive a portion of an interlocking component such that the interlocking component does not significantly move in a horizontal or vertical direction.

Figure 6:
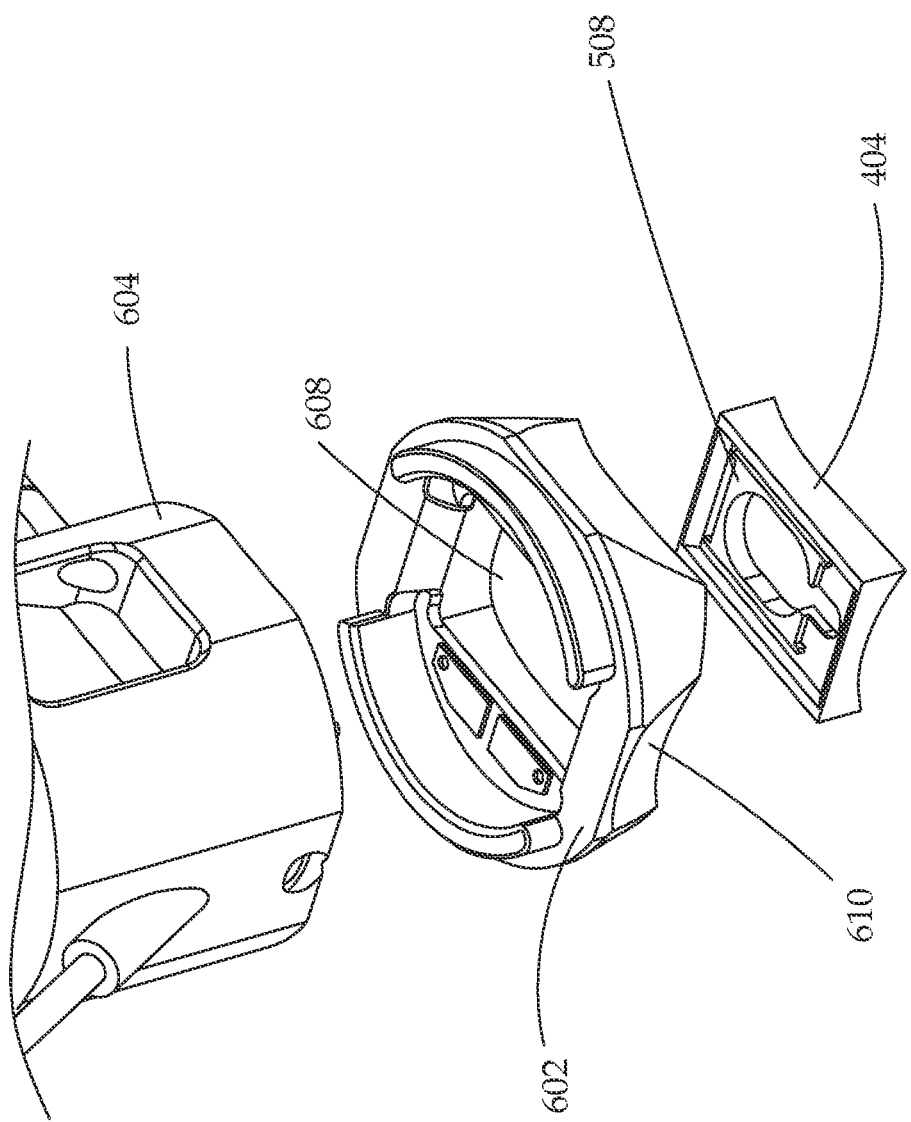
FIG. 6 illustrates an exploded view of a tissue anchor and sensor assembly, according to certain embodiments of the present disclosure.

FIG. 6 illustrates an example interlock component 602 that may mate with a tissue anchor 404 using a securing mechanism, such as the attachment structure 508 described with reference to FIG. 5.

An interlock component 602 can include a cavity 608 of a size and shape capable of accepting the tissue anchor 404 in whole or in part. Advantageously, the cavity 608 may serve as a primary or additional securing mechanism for the securing a sensor head 604 to a tissue anchor 404. However, other securing mechanisms are also possible and a sensor head 604 and tissue anchor 404 may be secured together with the aid of the interlock component 602 using any number of securing mechanisms, such as those described above.

The interlock component 602 may have one or more surfaces 610 of a similar curvature to the curvature of a surface of the tissue anchor 600. The curvature of the surfaces of the interlock component 602 and tissue anchor 404 can be of similar curvature to that of the area of the measured tissue site. For example, the tissue site may be a finger nail and the curvature of can follow the approximate curvature of the finger nail. In some examples, the curvature can be specific to the curvature of the tissue site of the user. For example, surfaces of the interlock component 602 and tissue anchor 404 can be molded, formed, or otherwise shaped according to the shape of the tissue site. In other examples, the curvature can be generic to the approximate curvature of the tissue site of the user. For example, surfaces of the interlock component 602 and tissue anchor 404 can be molded, formed, or otherwise shaped according to the approximate curvature of an adult human finger nail where the tissue site is a finger nail.

An interlock component 602 may be configured to couple to or be a part of a sensor head 604. Additionally or alternatively, the interlock component 602 may be a part of a system or device for receiving a tissue site at a sensor device. The interlock component 602 may be interchangeable such that more than one tissue anchor 404 may mate to a sensor head 604 or more than one sensor head 604 may mate to a tissue anchor 404. For example, a sensor head, such as a Raman sensor head, may have a unique footprint or geometry, differing from a different sensor head, such as an absorbance sensor head. Additionally, a tissue site may have a unique geometry. For example, a thumbnail may have a different curvature and area than a ring fingernail. An interlock component 602 may be configured to attach to a particular sensor head, such as a Raman sensor and a particular tissue site, such as an index finger. If a user desires to place the Raman sensor on their ring finger instead of their index finger, instead of reconfiguring the Raman sensor head, an interlock component 602 may be replaced that may be configured for placement on the ring finger. In another example, a user may desire to utilize a different sensor at the same tissue site, such as a Raman sensor instead of an absorbance sensor. The user may thus replace the interlock component 602 such that the Raman sensor may mate with the tissue anchor as opposed to the absorbance sensor.

Figure 7:
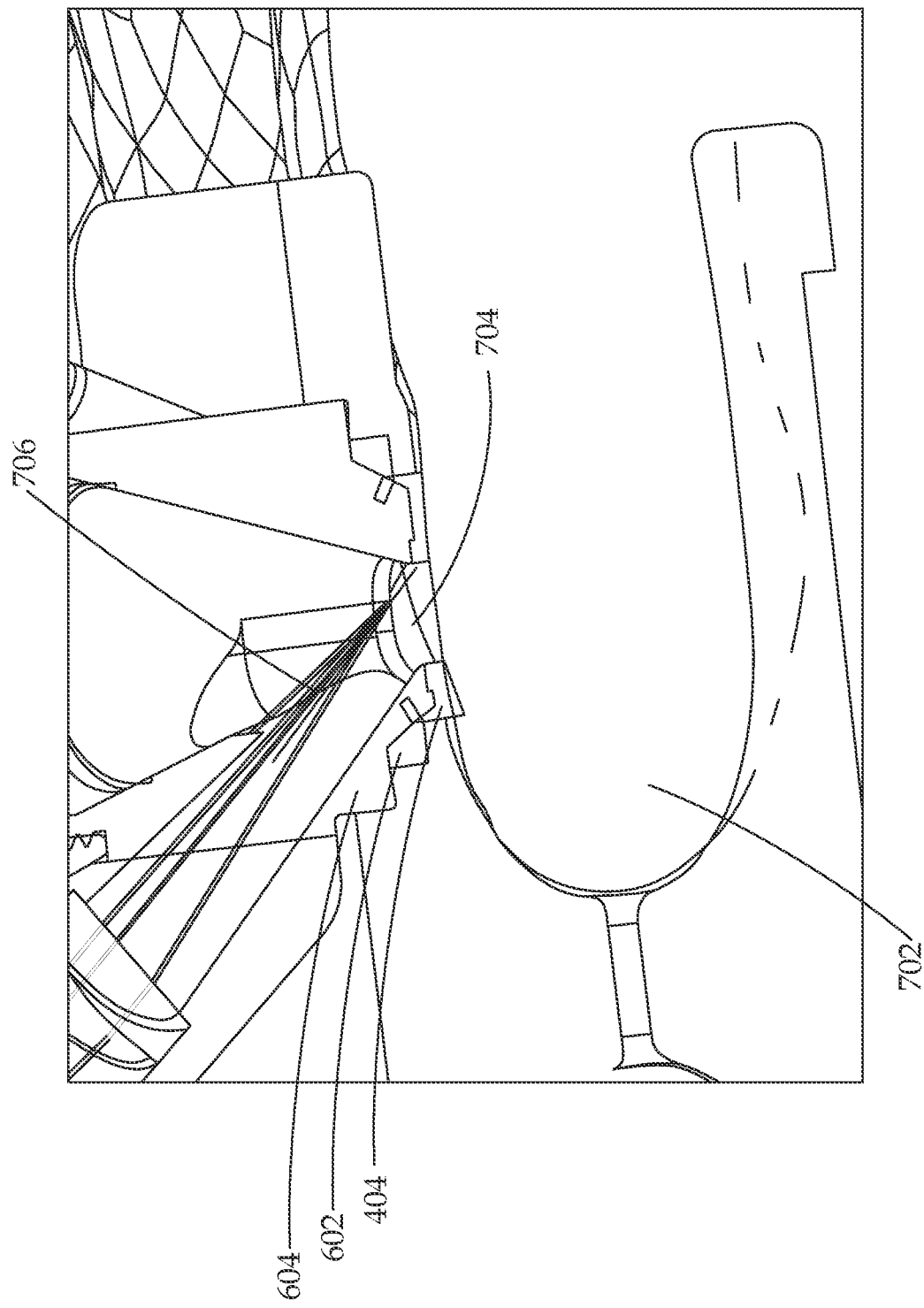
FIG. 7 shows a cross-section of an illustrative implementation of a tissue anchor and sensor assembly, according to certain embodiments of the present disclosure.

FIG. 7 illustrates a cross-section example of an assembled tissue scanning setup for an example tissue anchor 404, interlocking component 602, and sensor head 604. In the illustrated example, a finger 702 having an attached tissue anchor 404 is inserted into a device housing the interlocking component 602 and/or the sensor head 604. An open area 704 of the tissue anchor 404 can allow for an optical path towards the tissue site 704 such that a sensor can probe the tissue site 702.

Example Method of Use

Figure 8:
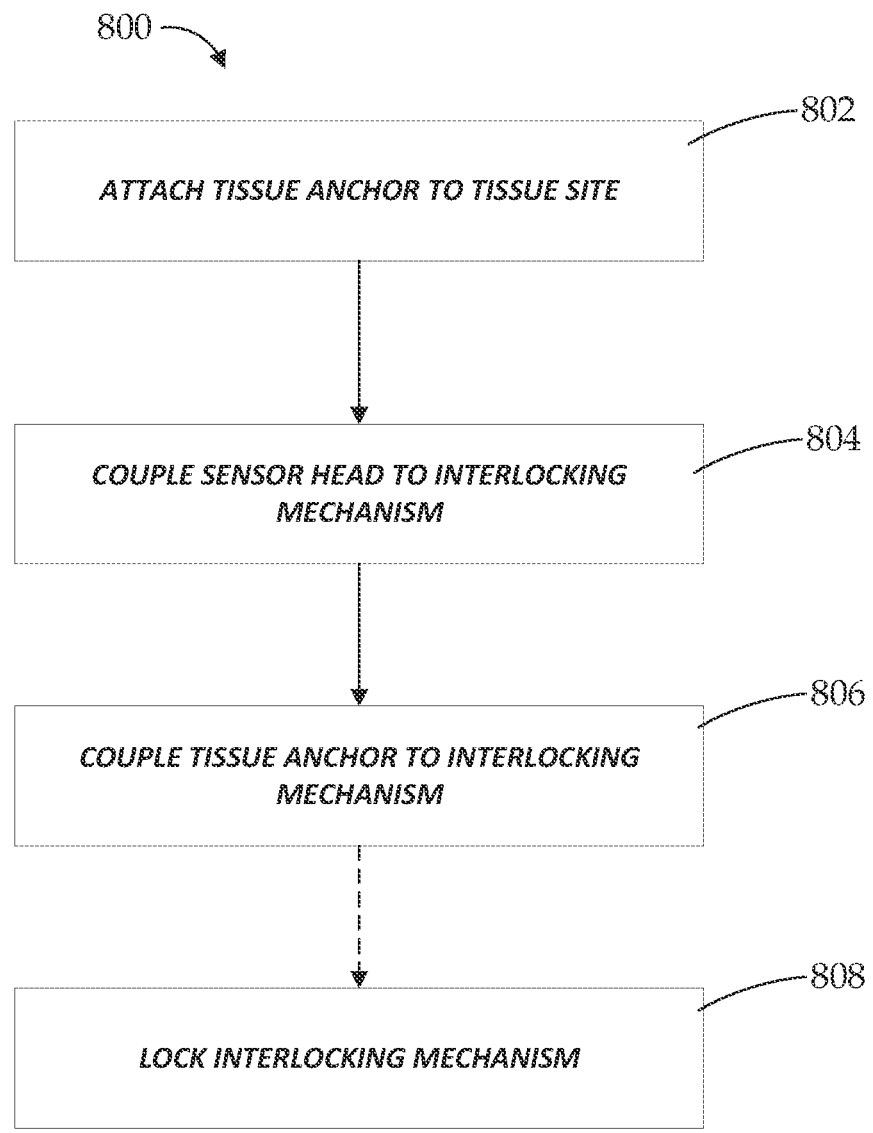
FIG. 8 shows a flow diagram illustrative of an example routine for using a tissue anchor, according to certain embodiments of the present disclosure.

FIG. 8 is a flow diagram of an exemplary method 800 of using the tissue anchor disclosed herein. The flow diagram begins at block 802 where the tissue anchor is attached to a tissue site. As disclosed above, the tissue anchor may be attached by any variety of means and the tissue site may be a finger or fingernail. Next, the interlocking mechanism is coupled with the sensor head and tissue anchor in blocks 804 and 806, respectively. Though blocks 804 and 806 appear in a certain order in the figure, it is to be understood that the figure is merely illustrative and that steps can occur in a different order or even simultaneously. Depending on the type of interlocking mechanism used, there may be an additional step 808 to lock the interlocking mechanism so that the tissue anchor cannot move horizontally or vertically.

Terminology

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figures. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A system for aligning a tissue site of a patient to a non-invasive sensor, comprising:
    a first anchoring component configured to couple to the tissue site of a patient, wherein the first anchoring component comprises:
        a first surface configured to couple to the tissue site;
        a first opening configured to allow the non-invasive sensor to perform a physiological measurement of the tissue site; and
        a securing component comprising a keyhole opening; and
    a second anchoring component associated with the non-invasive sensor such that, when the second anchoring component is coupled to the securing component, the sensor is secured to disallow horizontal movement relative to the tissue site, the second anchoring component comprising a first anchoring portion having a first diameter and a second anchoring portion having a second diameter, wherein the first diameter is greater than the second diameter, and wherein the first anchoring portion is positioned closer to the tissue site than the second anchoring portion when the second anchoring component is coupled to the securing component,
    wherein the keyhole opening comprises a first keyhole portion and a second keyhole portion, the first keyhole portion having a width greater than the first diameter, the second keyhole portion having a width less than the first diameter.

2. The system of claim 1, wherein the first surface is configured to couple to the tissue site using an adhesive.

3. The system of claim 2, wherein the adhesive is configured to couple the first surface to the tissue site for a period comprising at least one day.

4. The system of claim 1, wherein the first surface comprises a curvature similar to that of the tissue site.

5. The system of claim 1, wherein the securing component comprises at least one wall of the keyhole opening having a first slope and wherein the second anchoring component comprises at least one wall having the first slope.

6. The system of claim 1, wherein the second anchoring component is configured to mate with a third anchoring component.

7. The system of claim 6, wherein the third anchoring component comprises a portion of the non-invasive sensor.

8. The system of claim 1, wherein the second anchoring portion is configured to fit snugly within the second keyhole portion.

9. The system of claim 1, wherein, when the second anchoring component and securing component are coupled, the non-invasive sensor is secured to disallow vertical movement relative to the tissue site.

10. The system of claim 1, wherein an interior surface of the securing component partially defines a first conical shape, and wherein a surface of the second anchoring component at least partially defines a second conical shape, the first diameter comprising the widest portion of the second conical shape.

11. The system of claim 10, wherein the interior surface of the securing component and the surface of the second anchoring component are configured to contact when the second anchoring component is secured to the securing component.

12. The system of claim 1, wherein the first anchoring component is configured to couple to a fingernail of the patient.

13. The system of claim 1, further comprising the non-invasive sensor, wherein the non-invasive sensor is a Raman sensor.

14. A method for aligning a tissue site to a sensor, comprising:
    attaching a first anchoring component to the tissue site, the first anchoring component comprising:
        a first surface configured to couple to the tissue site;
        a first opening configured to allow the sensor to perform a physiological measurement of the tissue site; and
        a securing component comprising a keyhole opening comprising a first keyhole portion and a second keyhole portion;
    connecting, by inserting a second anchoring component through a first keyhole portion of the keyhole opening, the first anchoring component to the second anchoring component attached to a sensor head, wherein the second anchoring comprises a first anchoring portion having a first diameter and second anchoring portion having a second diameter, wherein the first diameter is greater than the second diameter, and wherein the second anchoring component is inserted through the keyhole opening such that the first anchoring portion is positioned closer to the tissue site than the second anchoring portion, and wherein the first keyhole portion has a width greater than the first diameter; and
    securing, by moving the second anchoring component to a second keyhole portion of the keyhole opening, the first and second anchoring components such that the sensor head is immobilized vertically relative to the tissue site and such that the sensor head is aligned with an opening in the first anchoring component, and wherein the second keyhole portion has a width less than the first diameter.

15. The method of claim 14, wherein the tissue site is a fingernail.

16. The method of claim 14, wherein moving the second anchoring component to the second keyhole portion the keyhole opening thereby mates a surface of the second anchoring portion to a surface of the first anchoring component.

17. The method of claim 14, wherein, when the first anchoring component and second anchoring component are secured, the sensor head is secured to disallow horizontal movement relative to the tissue site.

18. The method of claim 14, wherein the sensor of the sensor head is a Raman sensor.

* * * * *